United States Patent
Schrier et al.

(10) Patent No.: US 6,329,429 B1
(45) Date of Patent: Dec. 11, 2001

(54) USE OF GABA ANALOGS SUCH AS GABAPENTIN IN THE MANUFACTURE OF A MEDICAMENT FOR TREATING INFLAMMATORY DISEASES

(75) Inventors: Denis Schrier, Ann Arbor; Charles Price Taylor, Jr., Chelsea, both of MI (US); Karin Nanette Westlund High, League City, TX (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/403,867
(22) PCT Filed: Jun. 24, 1998
(86) PCT No.: PCT/US98/13107
 § 371 Date: Oct. 25, 1999
 § 102(e) Date: Oct. 25, 1999
(87) PCT Pub. No.: WO98/58641
 PCT Pub. Date: Dec. 30, 1998

Related U.S. Application Data
(60) Provisional application No. 60/050,736, filed on Jun. 25, 1997.

(51) Int. Cl.$^7$ .................................................. A01N 37/12
(52) U.S. Cl. .................... 514/561; 514/729; 560/122; 560/123; 562/504; 562/505; 562/507
(58) Field of Search .................... 514/561, 729; 560/122, 123; 562/504, 505, 507

(56) References Cited

U.S. PATENT DOCUMENTS
| | | | |
|---|---|---|---|
| 4,024,175 | 5/1977 | Satzinger et al. | 260/468 J |
| 5,518,730 | * 5/1996 | Fuisz . | |
| 5,563,175 | 10/1996 | Silverman et al. | 514/561 |

FOREIGN PATENT DOCUMENTS
| | | |
|---|---|---|
| JP60036413A | 2/1985 | (GB) . |
| 98/03167 | 1/1998 | (WO) . |
| 98/17626 | 4/1998 | (WO) . |

* cited by examiner

*Primary Examiner*—Gary Geist
*Assistant Examiner*—Robert W. Deemie
(74) *Attorney, Agent, or Firm*—Charles W. Ashbrook; Claude F. Purchase, Jr.

(57) ABSTRACT

GABA analogs such as gabapentin and pregabalin are useful to prevent and treat inflammatory diseases.

10 Claims, 9 Drawing Sheets

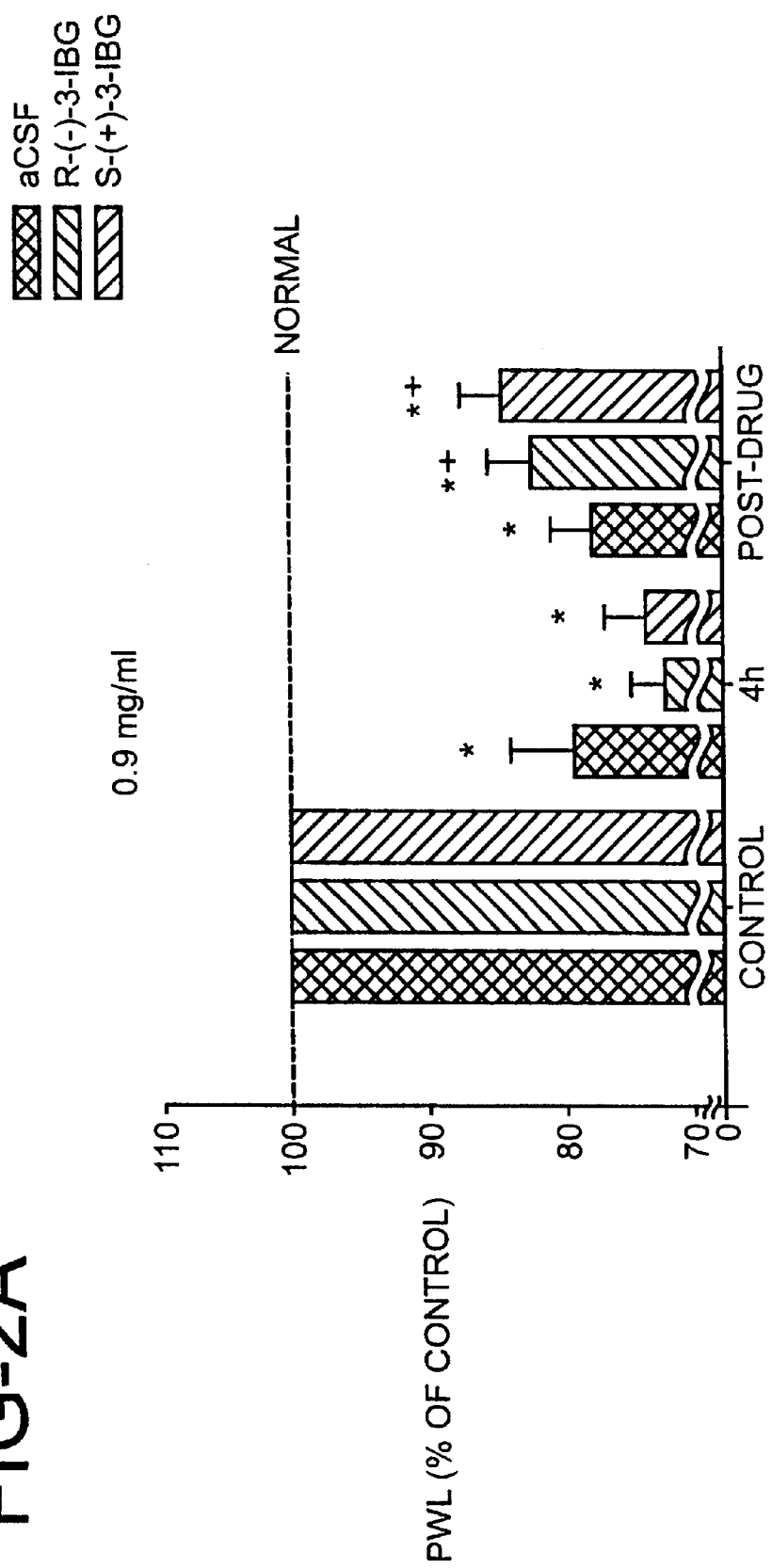

USE OF GABA ANALOGS SUCH AS GABAPENTIN IN THE MANUFACTURE OF A MEDICAMENT FOR TREATING INFLAMMATORY DISEASES

CROSS REFERENCE TO RELATED APPLICATIONS

This application was filed under 35 U.S.C. §371 from PCT/US98/13107 filed Jun. 24, 1998, which claims benefit of priority from U.S. provisional application No. 60/050,736 filed Jun. 25, 1997.

This invention was made in part with United States Government support under Grant No. IR01NS32778-01A1 administered by the National Institute of Health. The Federal Government may own certain rights in the invention.

FIELD OF THE INVENTION

This invention relates to a method for treating inflammatory diseases by administering a gamma-aminobutyric acid (GABA) analog.

BACKGROUND OF THE INVENTION

Inflammatory diseases are characterized by a complex series of histological events, including dilatation of arterioles, capillaries, and venules, with increased permeability and blood flow; exudation of fluids, including plasma proteins; and leukocytic migration into the inflammatory focus. Many forms of inflammation are localized protective responses elicited by injury or destruction of tissues, which serves to destroy, dilute, or wall off both the injurious agent and the injured tissue. The inflammatory response itself is also responsible for pathologic tissue damage. Arthritis is a particularly devastating inflammatory disease, generally affecting older people, and is characterized by the inflammatory lesions being primarily confined to articular joints. The disease is marked by pain, heat, redness, swelling, and tissue destruction. Rheumatoid arthritis is a chronic systemic disease of the joints, marked by inflammatory changes in the synovial tissue and articular structures, and by atrophy and rarefaction of the bones. This form of inflammatory disease generally progresses to deformity and ankylosis.

Numerous anti-inflammatory treatments are known and commonly used. The most common are the nonsteroidal anti-inflammatory agents such as naproxen, diflunisal, mefenamic acid, and ketorolac tromethamine. These agents generally are used to treat short term mild inflammation and pain. More severe inflammatory disease, such as arthritis, are treated with steroidal hormones and glucocorticoids, for example prednisolone, hydrocortisone acetate, and betamethasone sodium phosphate.

Because many of the anti-inflammatory agents are only short acting, and often produce severe side effects, the need for new therapies continue. We have now discovered that compounds which are analogs of gamma aminobutyric acid (GABA) are useful to treat inflammatory diseases. All that is required to prevent or treat the inflammatory disease according to this invention is to administer to a subject in need of treatment an anti-inflammatory amount of a GABA analog.

Several GABA analogs are known. Gabapentin, a cyclic GABA analog, is now commercially available and extensively used clinically for treatment of epilepsy and neuropathic pain. Such compounds are described in U.S. Pat. No. 4,024,175. Another series of GABA analogs is described in U.S. Pat. No. 5,563,175.

SUMMARY OF THE INVENTION

This invention provides a method for preventing and treating inflammatory diseases comprising administering to a subject suffering from such disease or suspected of developing such disease and in need of treatment an effective amount of a GABA analog. A preferred embodiment utilizes a cyclic amino acid compound of Formula I

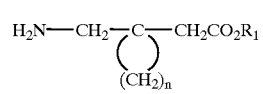

wherein $R_1$ is hydrogen or lower alkyl and n is an integer of from 4 to 6, and the pharmaceutically acceptable salts thereof. An especially preferred embodiment utilizes a compound of Formula I where $R_1$ is hydrogen and n is 5, which compound is 1-(aminomethyl)-cyclohexane acetic acid, known generically as gabapentin. Other preferred GABA analogs have Formula I wherein the cyclic ring is substituted, for example with alkyl such as methyl or ethyl. Typical of such compounds include (1-aminomethyl-3-methylcyclohexyl) acetic acid, (1-aminomethyl-3-methylcyclopentyl) acetic acid, and (1-aminomethyl-3,4-dimethylcyclopentyl) acetic acid.

In another embodiment, the anti-inflammatory method of the invention utilizes a GABA analog of Formula II

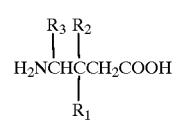

or a pharmaceutically acceptable salt thereof, wherein
$R_1$ is a straight or branched alkyl of from 1 to 6 carbon atoms, phenyl, or cycloalkyl of from 3 to 6 carbon atoms;
$R_2$ is hydrogen or methyl; and
$R_3$ is hydrogen, methyl, or carboxyl.

Diastereomers and enantiomers of compounds of Formula II can be utilized in the invention.

An especially preferred method of the invention employs a compound where $R_2$ and $R_3$ are both hydrogen, and $R_1$ is —$(CH_2)_{0-2}$-i $C_4H_9$ as an (R), (S), or (R,S) isomer.

A more preferred embodiment of the invention utilizes 3-aminomethyl-5-methyl-hexanoic acid, and especially (S)-3-(aminomethyl)-5-methylhexanoic acid, now known generically as pregabalin. Pregabalin is also known as "CI-1008" and "S-(+)-3-IBG." Another preferred compound of Formula II is 3-(1-aminoethyl)-5-methylhepanoic acid.

DETAILED DESCRIPTION OF THE INVENTION

As noted above, the method of this invention utilizes any GABA analog. A GABA analog is any compound derived from or based upon gamma-aminobutyric acid, and causes an anti-inflammatory effect in accordance with this invention. The compounds are readily available, either commercially, or by synthetic methodology well-known to those skilled in the art of organic chemistry. The preferred GABA analogs to be utilized in the method of this invention are cyclic amino acids of Formula I. These are described in U.S. Pat. No. 4,024,175 which is incorporated herein by reference. Another preferred method utilizes the GABA analogs of Formula II, and these are described in U.S. Pat. No. 5,563,175 which is incorporated herein by reference.

All that is required to practice the anti-inflammatory method of this invention is to administer a GABA analog in an amount that is effective to prevent or treat the inflammatory condition. Such anti-inflammatory amount will generally be from about 1 to about 300 mg per kg of subject body weight. Typical doses will be from about 10 to about 5000 mg per day for an adult subject of normal weight.

Pharmaceutical compositions of a GABA analog or its salts are produced by formulating the active compound in dosage unit form with a pharmaceutical carrier. Some examples of dosage unit forms are tablets, capsules, pills, powders, aqueous and nonaqueous oral solutions and suspensions, and parenteral solutions packaged in containers containing either one or some larger number of dosage units and capable of being subdivided into individual doses. Some examples of suitable pharmaceutical carriers, including pharmaceutical diluents, are gelatin capsules; sugars such as lactose and sucrose; starches such as corn starch and potato starch, cellulose derivatives such as sodium carboxymethyl cellulose, ethyl cellulose, methyl cellulose, and cellulose acetate phthalate; gelatin; talc; stearic acid; magnesium stearate; vegetable oils such as peanut oil, cottonseed oil, sesame oil, olive oil, corn oil, and oil of theobroma; propylene glycol, glycerin; sorbitol; polyethylene glycol; water; agar; alginic acid; isotonic saline, and phosphate buffer solutions; as well as other compatible substances normally used in pharmaceutical formulations. The compositions to be employed in the invention can also contain other components such as coloring agents, flavoring agents, and/or preservatives. These materials, if present, are usually used in relatively small amounts. The compositions can, if desired, also contain other therapeutic agents commonly employed to treat inflammation, for example, aspirin, naprosyn, and similar anti-inflammatory agents.

The percentage of the active ingredients in the foregoing compositions can be varied within wide limits, but for practical purposes it is preferably present in a concentration of at least 10% in a solid composition and at least 2% in a primary liquid composition. The most satisfactory compositions are those in which a much higher proportion of the active ingredient is present, for example, up to about 95%.

Routes of administration of the GABA analog or its salts are oral or parenteral. For example, a useful intravenous dose is between 5 and 50 mg, and a useful oral dosage is between 20 and 800 mg. The dosage is within the dosing range used in treatment of inflammatory diseases such as arthritis, or as would be determined by the needs of the patient as described by the physician.

A unit dosage form of the GABA analog to be used in this invention may also comprise other compounds useful in the therapy of inflammatory diseases.

The advantages of using the compounds of Formula I and II, especially gabapentin and pregabalin, in the instant invention include the relatively nontoxic nature of the compounds, the ease of preparation, the fact that the compounds are well-tolerated, and the ease of IV and oral administration of the drugs. Further, the drugs are not metabolized in the body.

The subjects as used herein are mammals, including humans.

The ability of GABA analogs to treat inflammatory diseases according to this invention has been established in several animal models of inflammation and arthritis.

Figure 1A:
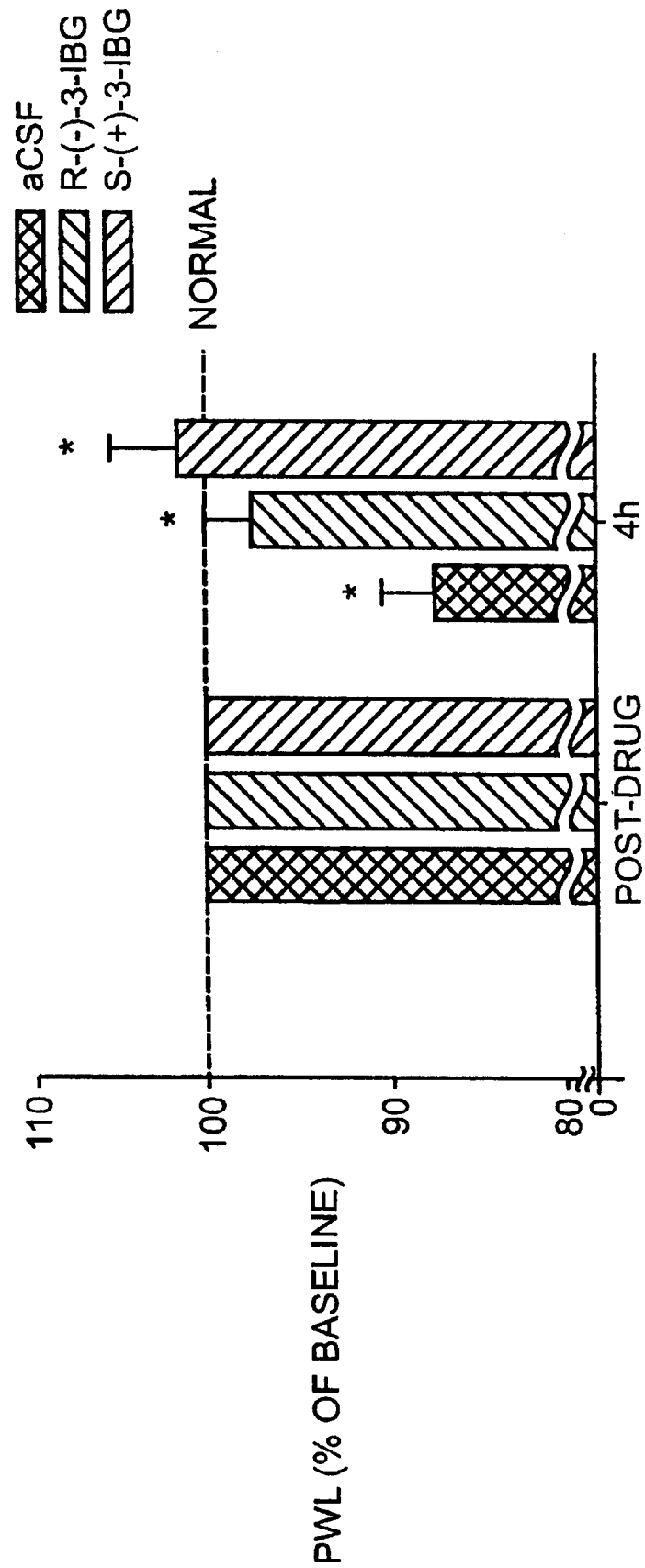
FIG. 1 shows the effects of pregabalin (designated as S-(+)-3-IBG), its corresponding R optical enantiomer R-(−)-3-isobutyl GABA (designated as R-(−)-3-IBG), and aCSF (artificial cerebrospinal fluid) on thermal PWL (paw withdrawal latency), on circumference of the knee joint, and on degree of pain in animals prior to development of acute arthritis.

The following detailed examples illustrate the specific anti-inflammatory activity of GABA analogs.

EXAMPLE 1

Gabapentin was evaluated in a streptococcal cell wall (SCW)-induced paw edema model. Female Lewis rats were sensitized to SCW (6 µg/rat) in the right tibiotalar joint on Day 0. Vehicle (0.5% hydroxypropylmethylcellulose/0.2% Tween 80) or drug (100 mg/kg, BID) was administered orally (10 mL/kg) beginning 1 hour before initiation of the delayed-type hypersensitivity reaction by systemic SCW (100 µg/rat) on Day 21, and given through Day 24. Assessment of hindpaw edema was determined on Days 22 through 25 by mercury plethysmometry.

Gabapentin was found to significantly inhibit swelling on Days 22, 23, 24, and 25 (58%, 77%, 83%, and 81%, respectively).

EXAMPLE 2

Pregabalin was evaluated in a similar assay and showed dramatic anti-inflammatory activity. The assay is a streptococcal cell wall (SCW) induced reactivation arthritis assay. Female Lewis rats were injected intra-articularly with 10 µL of 100 p fraction peptidoglycan polysaccharide (PG-PS) suspended in phosphate buffered saline (PBS). The contralateral joints were injected with PBS as control. Systemic challenge with 100 µg of PG-PS was given via the tail vein 21 days after the initial inoculation. The animals were dosed orally three times a day with pregabalin (3, 10, and 30 mg/kg) on a 12-hour cycle for 72 hours. The first dose was given 1 hour before the systemic challenge.

Systemic challenge on Day 21 of previously sensitized animals with SCW resulted in acute swelling in the sensitized ankle. The volume of the ankles increased by out 0.5 mL within 72 hours. Pregabalin at 10 and 30 mg/kg dose dependently attenuated the increase in edema up to 40% during the 72-hour observation period. The results are present in Table 1.

TABLE 1

Effect of Pregabalin on Ankle Swelling
(Days 0–20 were sensitization period)

Swelling (delta edema, mL)

| Day 21 PG-PS Challenge | Day 22 | Day 23 | Day 24 | Pregabalin oral (mg/kg) |
|---|---|---|---|---|
| 0 | 0.20 | 0.45 | 0.50 | 0 (n = 6) |
| 0 | 0.12 | 0.38 | 0.50 | 3.0 (n = 6) |

TABLE 1-continued

Effect of Pregabalin on Ankle Swelling
(Days 0–20 were sensitization period)

Swelling (delta edema, mL)

| Day 21 PG-PS Challenge | Day 22 | Day 23 | Day 24 | Pregabalin oral (mg/kg) |
|---|---|---|---|---|
| 0 | 0.04 | 0.25 | 0.31 | 10.0 (n = 4) |
| 0 | 0.06 | 0.20 | 0.21 | 30.0 (n = 6) |

The foregoing assay establishes that GABA analogs such as gabapentin and pregabalin are effective anti-inflammatory agents and cause a reduction in swelling of the type encountered in patients suffering from arthritis.

EXAMPLE 3

Pregabalin (which is an S-isomer, and is also known as CI-1008, and as S-(+)-3-IBG) was also evaluated in the following anti-inflammatory test, along with the corresponding R-isomer, (R)-3-(aminomethyl)-5-methyl-hexanoic acid (also referred to as R-(−)-3-IBG). Acute experimental arthritis was induced in rats by injection of kaolin and carrageenan into the knee joint. The inflammatory agent, carrageenan, causes plasma extravasation and edema following the release of neuropeptides and other inflammatory mediators into the joint cavity. Concomitant with the injury to the joint tissue, both peripheral and central sensitization occurs, which is manifested in the awake rat as hyperalgesia, which can be easily quantified by measuring a reduction in paw withdrawal latencies to a radiant heat source. Both pregabalin and its R-stereoisomer (R-(−)-3-IBG) were administered before inflammation was induced, and after the inflammation was developed.

Thirty-six male Sprague-Dawley rats (235–380 g) were anesthetized with sodium pentobarbital (Nembutal; 50 mg/kg$^{-1}$ i.p.). A microdialysis fiber (200 µm o.d., 45000 MW Cut-off, Hospal AN69) was coated with epoxy resin, except for a 2 mm section. A small midline incision was made in the back at the level of the last rib. The muscle was then removed from around the $T_{12}$ vertebra and a hole drilled in both lateral aspects. The microdialysis fiber was then passed transversely through the dorsal horn of the spinal cord between lumbar segments $L_4$–$L_6$ so that the permeable 2 mm of the fiber lay in the dorsal horn. The microdialysis fiber was connected to $PE_{20}$ tubing (Becton and Dickson) which was then tunneled under the skin to the nape of the neck. The fiber was stabilized with dental cement. Artificial cerebrospinal fluid (aCSF) was pumped through the tubing at a rate of 5 µL/min for 1 hour before the $PE_{20}$ was sealed and the animals allowed to recover.

As a measure of thermal hyperalgesia, animals were tested for paw withdrawal to radiant heat. On the day following fiber placement, animals were housed in small lucite cubicles on an elevated glass plate. Radiant heat was applied to the plantar surface of the heel of the hindpaw until the rat lifted the paw. The time at which this occurred was considered the paw withdrawal latency (PWL). Both paws were tested independently at 5-minute intervals, for a total of 5 trials. A mean of these five readings was used as the PWL. In pre-treatment rats, PWL was measured before administration of any GABA analogs (baseline) and after the GABA analog had been infused for 1.5 hours, at which time kaolin and carrageenan was injected into the knee joint. PWL was measured for a final time 4 hours after arthritis induction. In the post-treatment group, the animals were tested before induction of arthritis in the knee joint (control), 4-hours post-induction, and 1.5 hours after of drug infusion, i.e. 5.5 hours after arthritis induction. A decrease in the PWL to radiant heat in an animal with knee joint inflammation is indicative of secondary hyperalgesia.

The circumference of the knee joint was also measured before injection of kaolin and carrageenan (control) using a flexible tape measure. The extent of guarding of the hindpaw was also noted after arthritis was induced. To quantify these changes, the animals were graded by a subjective pain rating scale (0–5), where: 0 is normal; 1 is curling of the toes; 2 is eversion of the paw; 3 is partial weight bearing; 4 is non-weight bearing and guarding; and 5 is avoidance of any contact with the hindlimb.

Induction of Arthritis

Rats were anesthetized briefly with sodium methohexital (Brevital; 60 mg/kg$^{-1}$ i.p.) after the control behavioral test (post-treatment group) or after infusion of the drug (pre-treatment group). The knee joint was then injected with 3% kaolin and 3% carrageenan suspended in sterile saline (0.1 mL; pH 7.4). The knee joint was then flexed manually until the rat awoke (approximately 5 minutes).

Administration of GABA Analogs

All GABA analogs were dissolved in an artificial cerebral spinal fluid solution (aCSF) (pH 7.4, adjusted by bubbling with 95% $CO_2$/5% $O_2$) and infused through the spinal cord at 5 µL/min$^{-1}$. The animals received either pregabalin, R-(−)-3-IBG, or aCSF. In the post-treatment group, the GABA analogs were infused at concentrations of 0.1, 0.9, and 10 mg/mL. In contrast, the pre-treatment group received a single dose of 10 mg/mL.

Statistical Analysis

The data was normally distributed. Statistical analyses were carried out using unpaired t-tests for comparison of differences between treatment groups at the same timepoint. Paired t-tests were used to compare before and after treatment within the same group. A P value of less than 0.05 was used to indicate significance. Data are expressed as means ±s.e.m. Tests were carried out using Statistica (Jandel Corporation).

Results

Effect of Pregabalin and its R-Isomer Infused Into the Spinal Cord Before the Development of Acute Arthritis Infusion of 10 mg/mL of pregabalin, its R-isomer, or aCSF into the dorsal horn of the spinal cord alone did not change PWL in the thermal hyperalgesia test when compared to baseline values. The PWL of the rats treated with aCSF before the induction of inflammation was significantly reduced at 4 hours after injection of kaolin and carrageenan (P<0.01, paired t-test), when compared to the value recorded immediately before injection. There was also a significant difference (P<0.05, unpaired t-test) between the injected limb and the uninjected limb at this time.

Figure 1B:
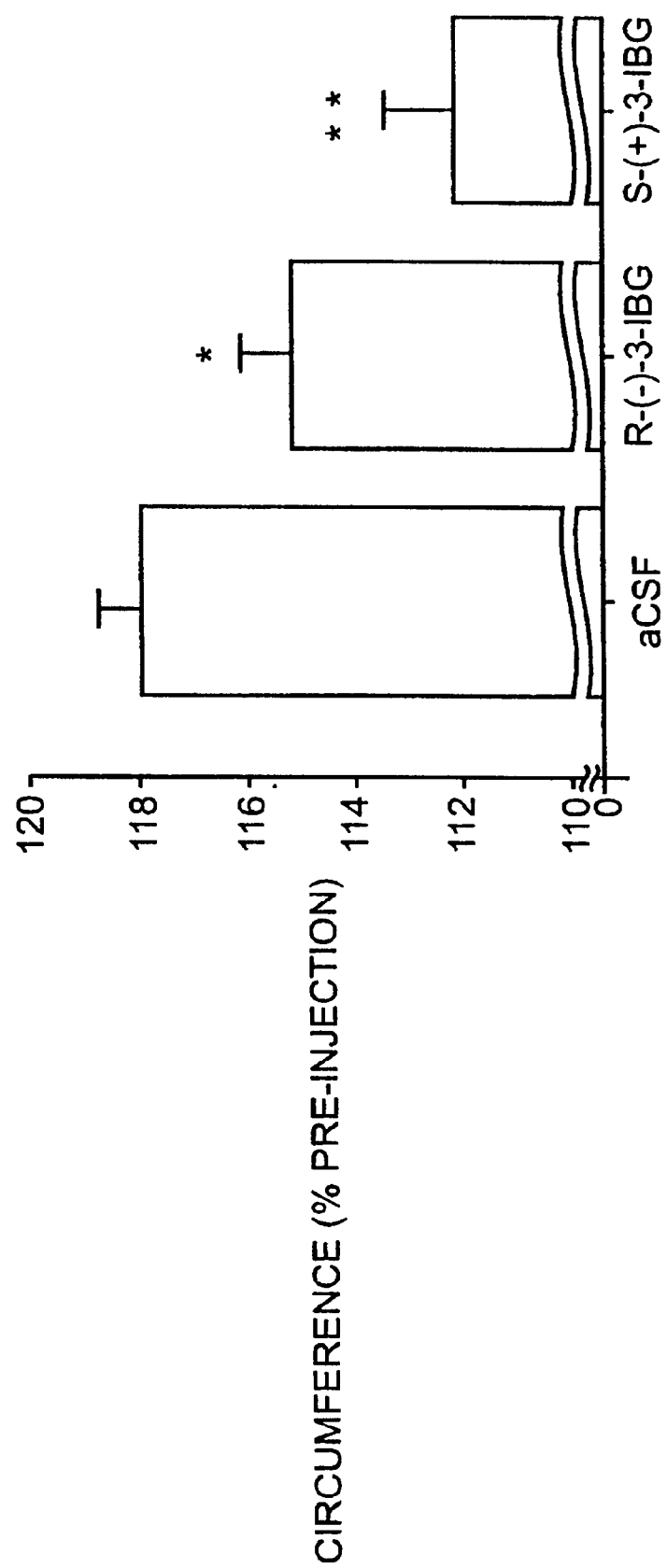
Figure 1C:
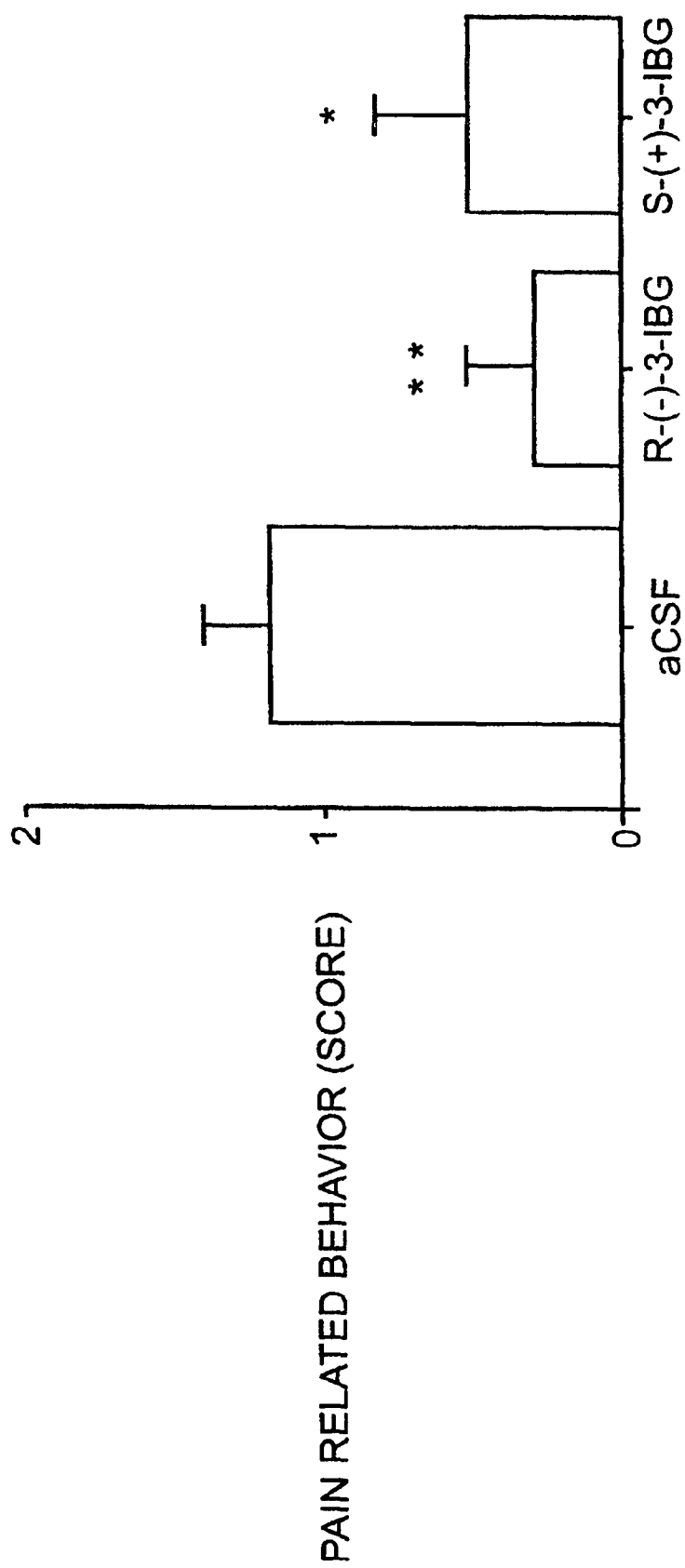

However, in the rats infused with a concentration of 10 mg/mL pregabalin or its R-isomer through the spinal cord for 1.5 hours before the injection of kaolin and carrageenan into the knee joint, no secondary thermal hyperalgesia was observed 4-hours post-injection (FIG. 1, top panel). No significant difference was observed between the PWL value recorded 4 hours after inflammation and that recorded prior to injection of kaolin and carrageenan, nor between the inflamed limb and the uninflamed limb 4 hours after injection of kaolin and carrageenan.

Infusion of pregabalin or its R-isomer into the spinal cord for 1.5 hours before the induction of arthritis also significantly reduced (P<0.05; unpaired t-test) the amount of swelling typical after injection of kaolin and carrageenan into the knee joint by approximately 30%, when compared to rats in which aCSF was infused (FIG. 1, middle panel). Further, pre-treatment with pregabalin or its R-isomer prevented the development of abnormal paw posture indicative of spontaneous pain (FIG. 1, bottom panel).

Figure 2B:
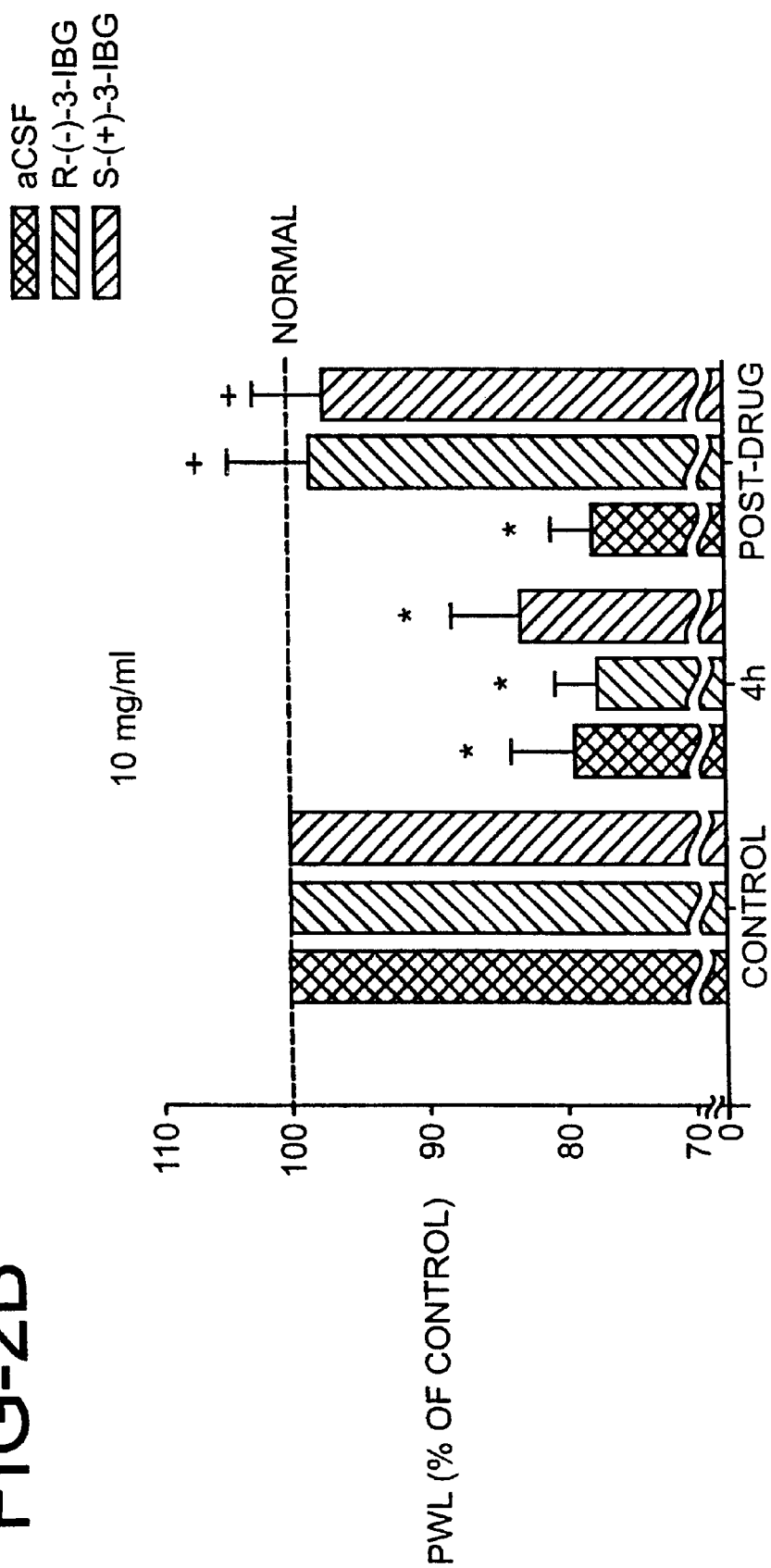
FIG. 2 shows the effects of 0.9 and 10 mg/mL doses of pregabalin, R-(−)-3-IBG, and aCSF on thermal paw withdrawal latencies, administered after development of acute arthritis.
Figure 3A:
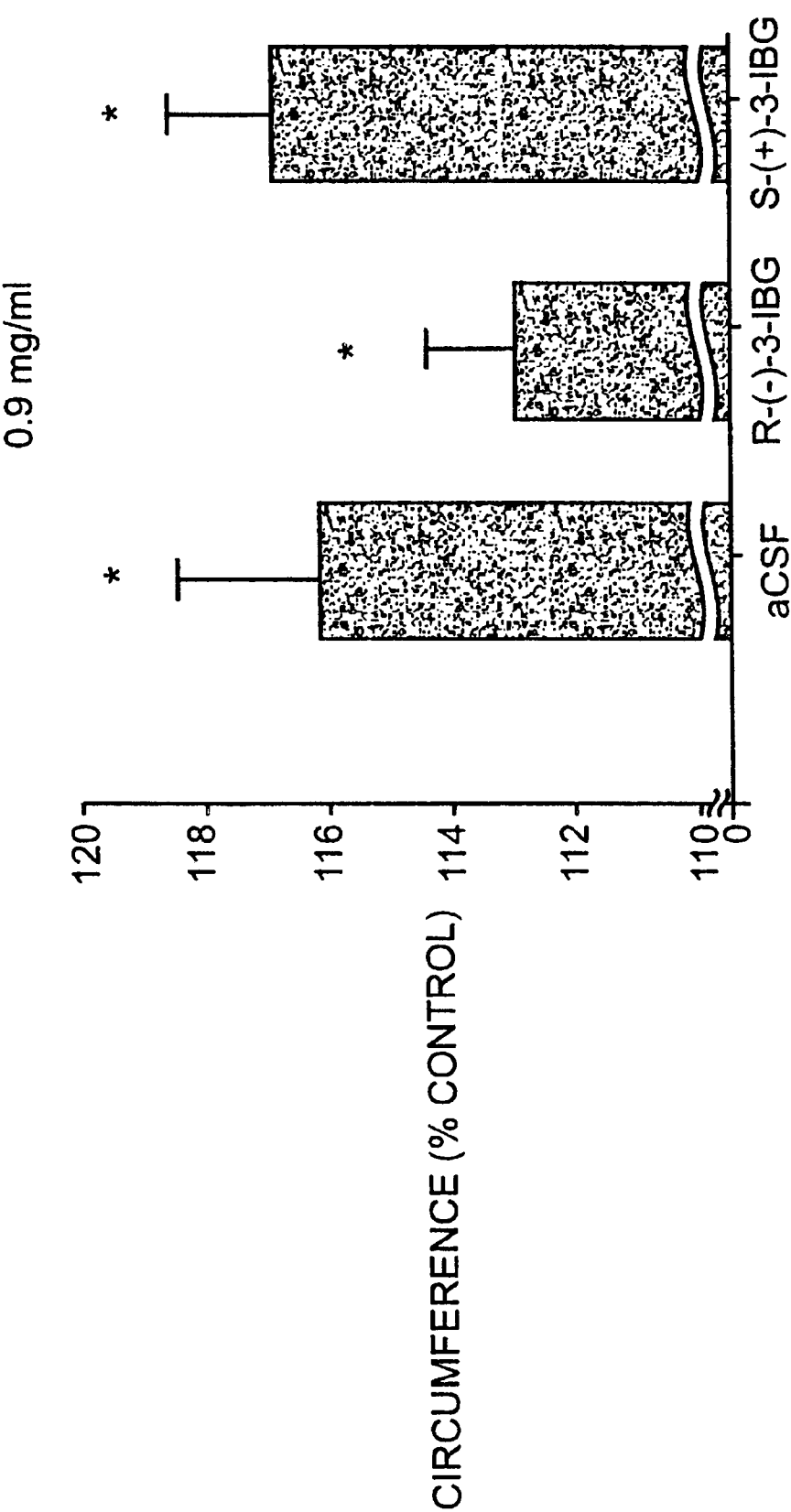
FIG. 3 shows the effects of 0.9 and 10 mg/mL of Pregabalin, R-(−)-3-IBG and aCSF on joint swelling, administered after development of acute arthritis.
Figure 3B:
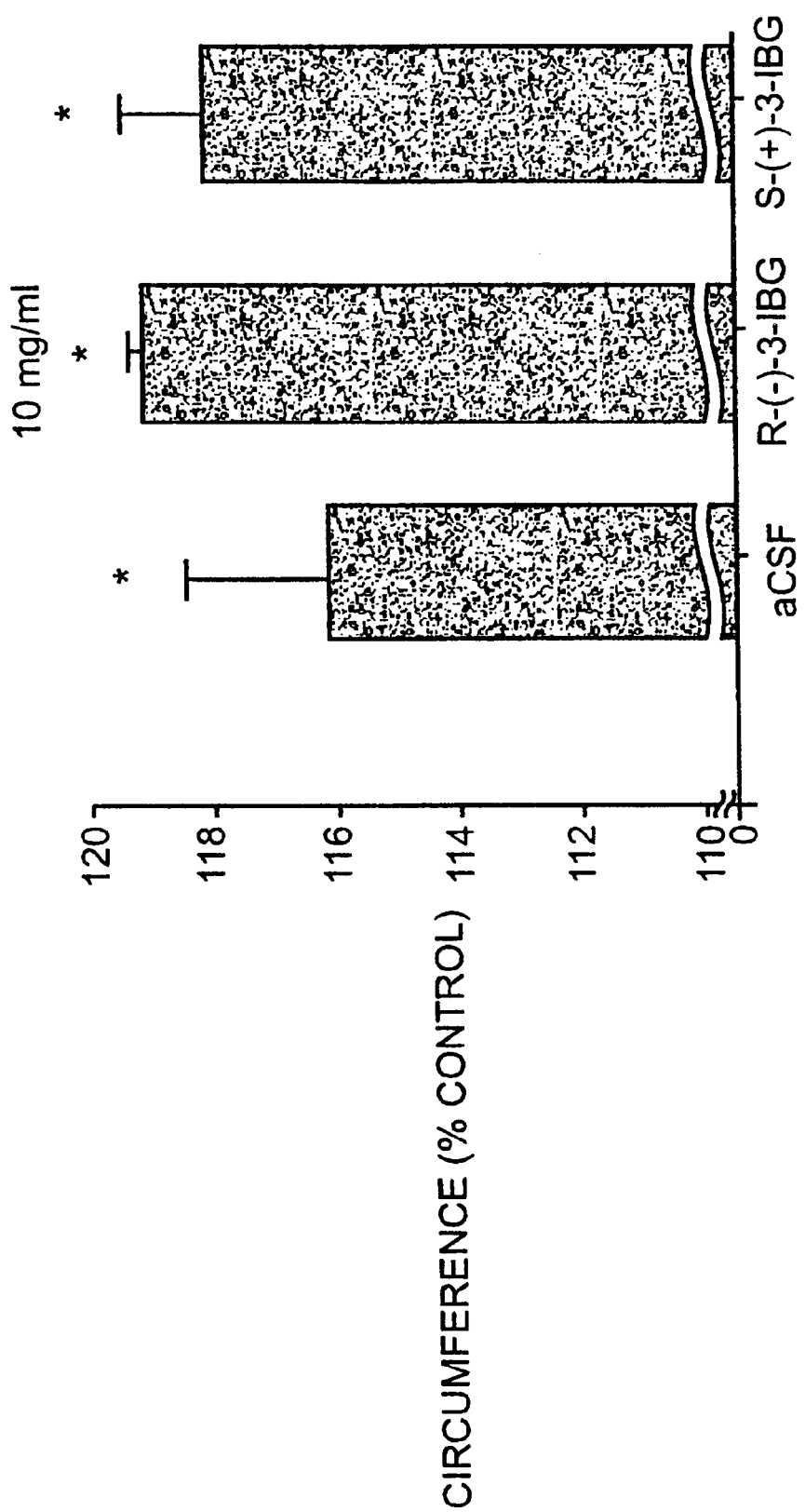
Figure 4A:
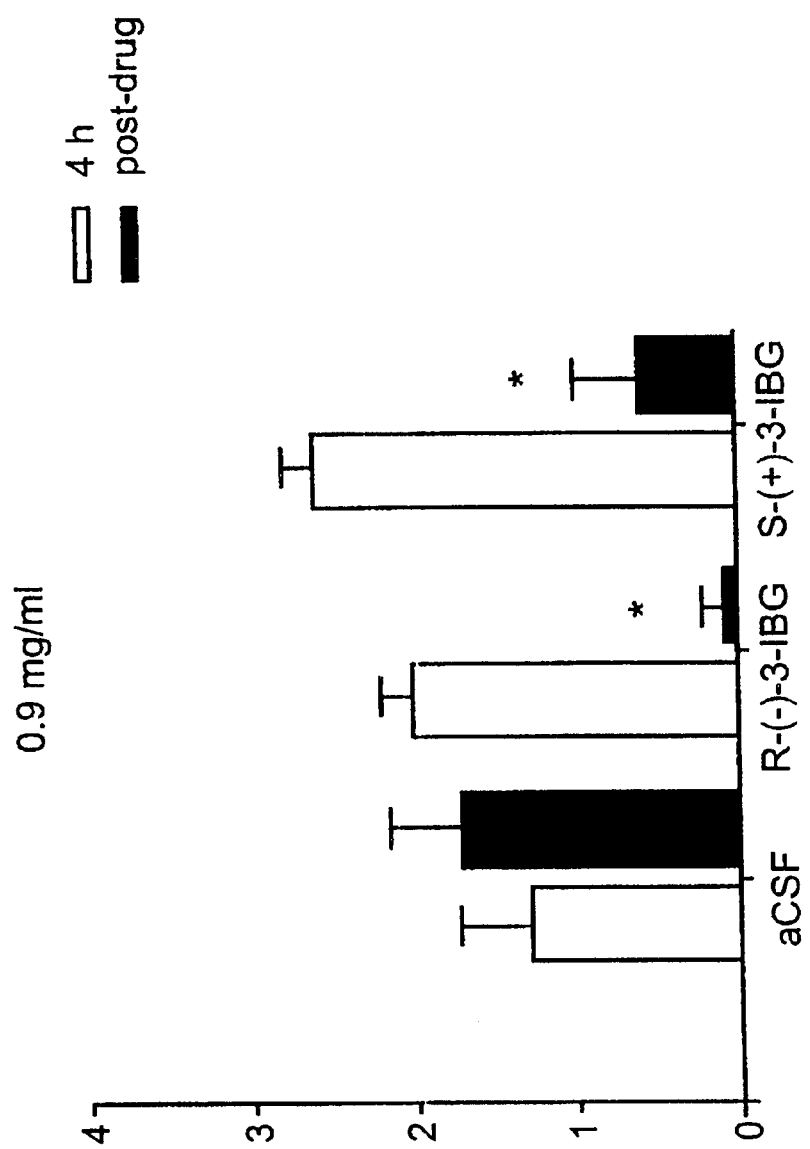
FIG. 4 shows the effects of 0.9 and 10 mg/mL of pregabalin, R-(−)-3-IBG and aCSF on pain-related behavior, when administered after development of acute arthritis.
Figure 4B:
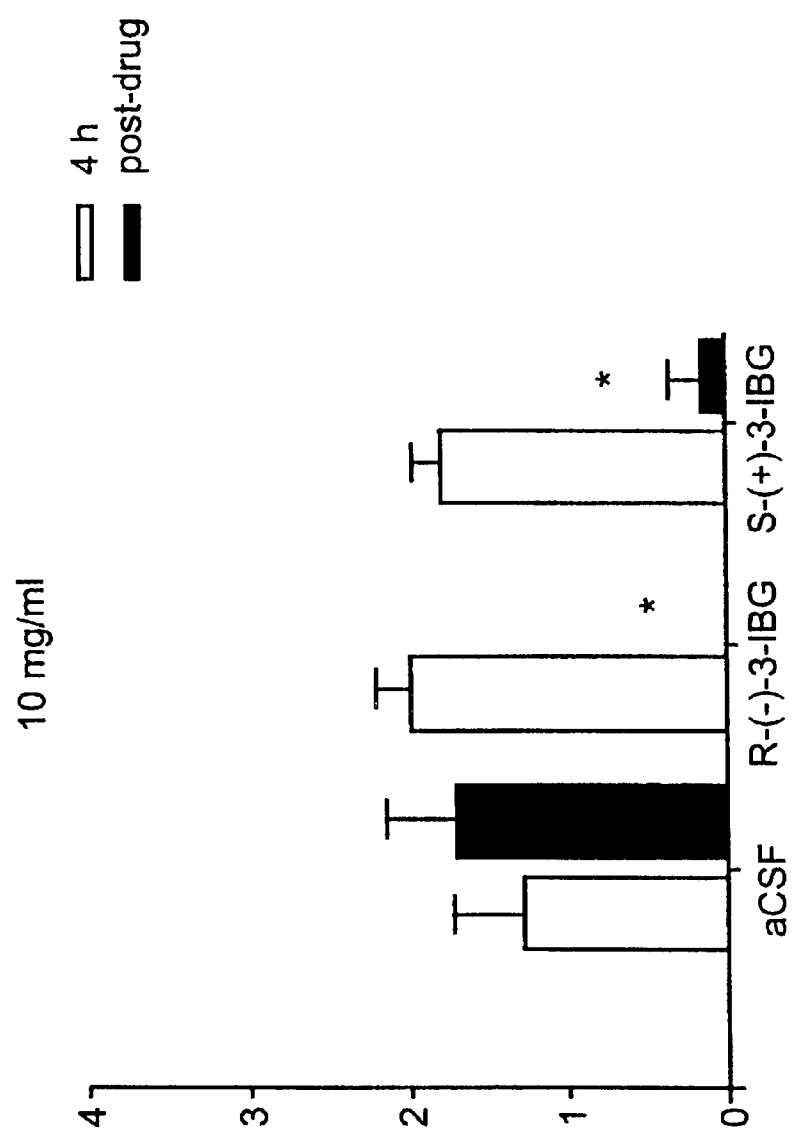

Effect of Pregabalin and its R-isomer Infused Into the Spinal Cord After the Development of Acute Arthritis Four hours after the induction of acute inflammation of the knee joint, there was a decrease in the PWL to radiant heat of the ipsilateral footpad, when compared to the control value, in all animals tested (n=30), indicating the presence of secondary hyperalgesia (FIG. 2). This decrease was significant (paired t-test, p<0.01). Four hours after inflammation of the knee joint, there was a significant increase in knee joint circumference compared to the measurement recorded immediately before injection of kaolin and carrageenan (P<0.05, paired t-test; FIG. 3). After inflammation, there was also a change in the rats' posture (decreased weight bearing upon the swollen limb, and curling of the toes) reflected by the increased spontaneous pain rating score given to the rats (FIG. 4, hollow bars).

The infusion of 0.9 mg/mL pregabalin or its R-isomer into the dorsal horn of the spinal cord reduced the thermal hyperalgesia at 5.5 hours (FIG. 2, upper panel). Although the PWL recorded after infusion of either drug was significantly different from that recorded 4 hours after inflammation, it was still significantly less than the control value. Pregabalin was more effective in reducing thermal hyperalgesia than its R-isomer. Infusion of a higher dose, 10 mg/mL, of pregabalin or its R-isomer, after inflammation of the knee joint, resulted in a return of the PWL to the control value (FIG. 2, lower panel). In contrast, infusion of aCSF into the dorsal horn did not reduce the thermal hyperalgesia; the PWL at 4 hours after inflammation and after aCSF infusion were not significantly different.

The spontaneous pain was also reduced by infusion of both doses of pregabalin and its R-isomer. After infusion of either isomer of the drug, the paw posture was almost normal, whereas after infusion of aCSF, curling of the toes and eversion of the paw were observed.

The results from these studies show that injection of kaolin and carrageenan into the knee joint of the rat results in an acute arthritis which is characterized by secondary thermal hyperalgesia, swelling of the knee joint, and spontaneous pain. Infusion of pregabalin and R-(−)-3-IBG into the dorsal horn of the spinal cord for 1.5 hours before the injection of kaolin and carrageenan reduced the amount of swelling observed, and blocked the secondary hyperalgesia and spontaneous pain. The GABA analogs are thus useful to treat inflammatory diseases, especially arthritis.

EXAMPLE 4

Gabapentin, another GABA analog, was evaluated in a similar assay and shown to be effective in both preventing and reversing the affects of kaolin/carrageenan knee joint inflammation, secondary heat hyperalgesia and spontaneous pain-related behaviors.

Methods

Thirty animals in two experimental groups were treated (1) prior to, and (2) after induction of experimental arthritis. Inflammation was induced within the knee joint by injection of kaolin/carrageenan. Gabapentin or aCSF was administered through a microdialysis fiber positioned in the dorsal horn for spinal treatment, or subcutaneously in the nape of the neck for systemic release. All experiments were carried out by an observer blind to the drug treatment.

Placement of Microdialysis Fibers

Sprague-Dawley rats (220–270 g) were anesthetized with sodium pentobarbital (nembutal, 50 mg/kg, i.p.). A microdialysis fiber (200 μm o.d., 45000 MW Cut-off, Hospal AN69) was coated with epoxy resin, except for a 2 mm section. In 24 animals, the microdialysis fiber was placed in the dorsal horn. A small midline incision was made in the skin over the $L_1$ vertebral level. The $L_1$ vertebra was cleared of muscle and a hole drilled in both sides of the lamina. The microdialysis fiber was then passed through the holes in the vertebrae and transversely through the dorsal horn of the spinal cord. The microdialysis fiber lay between $L_4$–$L_6$ segments with the permeable 2 mm of the fiber in the dorsal horn. The microdialysis fiber was connected to $PE_{20}$ tubing (Becton Dickinson) which was tunneled under the skin to the nape of the neck. The connecting joint between the microdialysis fiber and PE20 tubing was stabilized with dental cement. The aCSF was pumped through the tubing at a rate of 5 μL/min for 1 hour before the $PE_{20}$ tubing was sealed, and the animal was allowed to recover for 24 hours. Once the rats were awake, they were examined for motor deficits; any rat which had motor deficits was excluded from the study. As a systemic control for drug administration in another 6 rats, the microdialysis fiber was implanted in the subcutaneous tissue at the nape of the neck.

Behavior Testing and Assessment of Arthritis

The PWL to noxious radiant heat was tested as a measure of thermal hyperalgesia. A decrease in the PWL in animals with knee joint inflammation was interpreted as indicative of secondary hyperalgesia. Since the radiant heat stimulus is applied to the plantar surface of the hindpaw at quite some distance from the inflamed knee joint, the measure reported represents secondary heat hyperalgesia.

On the day following fiber placement, animals were housed in small lucite cubicles on an elevated glass plate. Radiant heat was applied to the plantar surface of the hindpaw until the rat lifted the paw. The time at which this occurred was considered the PWL. Both paws were tested independently at 5-minute intervals for a total of five trials. A mean of these five readings was used as the PWL for each time points. In pretreatment rats (n=12), PWL was measured before administration of any drugs (baseline), after the drug had been infused for 1.5 hours (post-drug), and 4 hours after arthritis. In the post-treatment group (n=18), the animals were tested before induction of arthritis in the knee joint (baseline), 4 hours after induction of arthritis, and 1.5 hours after drug infusion, i.e., 5.5 hours after arthritis induction.

The pain-related behavior, the extent of guarding of the hindpaw of the arthritis limb, was scored by two independent observers. To quantify these changes, the animals were graded by a subjective pain rating scale (0–5) where: 0 is normal, 1 is curling of the toes, 2 is eversion of the paw, 3 is partial weight bearing, 4 is non-weight bearing and guarding, and 5 is avoidance of any contact with the hindpaw.

The circumference of the knee joint was also measured using a flexible tape measure before induction of arthritis (baseline), 4 hours after induction of arthritis (pretreatment and posttreatment group), and 1.5 hours after drug infusion in the posttreatment group (5.5 hours after induction of arthritis).

Induction of Arthritis

Rats were anesthetized briefly with methohexital sodium (Brevital sodium, 60 mg/kg i.p.) after baseline behavior test (post-treatment group) or after infusion of the drug (pretreatment group). The knee joint was then injected with 0.1 mL of 3% kaolin and 3% carrageenan suspended in sterile saline, and was flexed manually until the rat awoke (approx. 5–10 min.).

Administration of Drug

The animal received either gabapentin or aCSF as a control. The gabapentin was dissolved in aCSF. Both gabapentin and aCSF were infused through the microdialysis fiber at a rate of 5 μL/minute. The pH of the gabapentin solution and aCSF were adjusted by bubbling with 95% $CO_2$/5% $O_2$ (about 7.4) before using.

The single dose of 10 mg/mL of gabapentin was used for the study.

Statistical Analysis

The results for each group were expressed as the average percent change from baseline±the standard error of the mean (s.e.m.). Paired t-tests were used to compare each animal's test responses to its own baseline (P<0.01).

Results

Baseline measures

The baseline PWL, spontaneous behavior, and knee joint circumference of all rats used in these studies were measured prior to infusion of the drug or vehicle through the spinal cord or subcutaneously (Table 2). The mean PWL and knee joint circumference were 10.52±0.39 sec and 5.26±0.03 cm, respectively. No spontaneous pain-related behaviors were noted and a score of zero given.

Consequent Changes with Joint Inflammation

In Table 2, the expected outcome in arthritic animals for all measures is presented. The data includes the combined measures for the aCSF arthritic control animals from both treatment groups. In the aCSF-treated arthritic control rats (n=12), 4 hours after injection of kaolin and carrageenan, the PWL to noxious radiant heat decreased to 76% of baseline value. This decrease was significant (paired t-test, p<0.01 ) and indicated the presence of secondary hyperalgesia.

In arthritic animals, there was a significant change in the hindpaw posture of the rat, indicative of spontaneous ongoing pain-related behavior. These postural changes, representing spontaneous ongoing pain-related behavior, were represented by a score of 1.25±0.13 (p<0.01). A significant 14% increase in knee joint circumference is noted compared to the baseline (paired t-test, p<0.01).

The Effect of Gabapentin Infusion Directly into the Spinal Cord Before Knee Joint Inflammation Gabapentin was effective in preventing the development of secondary hyperalgesia responses to the applied radiant heat. Gabapentin or aCSF were infused through the microdialysis fiber into the spinal cord before the knee joint was injected with kaolin and carrageenan. After 1.5 hours of spinal drug infusion, there were no significant changes of the PWL to the radiant heat compared to the baseline (Table 3). Four hours after injection of the knee joint with kaolin and carrageenan, the PWL response to radiant heat and the posture of the hindpaw with arthritis were not significantly changed from non-arthritic baseline. In contrast, the aCSF-treated animals had a significant reduction in their PWL responses, and demonstrated significant spontaneous pain-related behaviors. The circumference of the inflamed joint was increased significantly 4 hours after arthritis, similar to the aCSF arthritic control rats. Thus, gabapentin was highly effective in preventing the development of secondary heat hyperalgesia and measures of spontaneous pain-related behaviors.

TABLE 3

Effects of Gabapentin Administered Prior to Inflammation

| Groups | Baseline (% of control) | PWL (1.5 h after drug infusion) | PWL (4 h after joint injection) | Behavior Score (4 h after joint inspection) | Circumference (4 h after joint injection) |
|---|---|---|---|---|---|
| Gabapentin (n = 6) | 100 | 105.18 ± 4.56 | 100.03 ± 4.37 | 0.67 ± 0.20 | 114.20 ± 1.53* |
| aCSF (n = 6) | 100 | 93.12 ± 6.31 | 74.47 ± 3.44* | 1.33 ± 0.2* | 114.87 ± 1.74* |

*p < 0.01.

Effect of Gabapentin Infusion into the Spinal Cord or Subcutaneously After Knee Joint Inflammation Post-treatment of arthritic animals with gabapentin reversed the secondary heat hyperalgesia and spontaneous pain-related behaviors when administered spinally. Two groups of animals received gabapentin in post-treatment studies (Table 4). One group of rats was infused with the drug through a microdialysis fiber implanted directly into the spinal cord; the other group received gabapentin systemically through a microdialysis fiber implanted subcutaneously at the nape of the neck.

Four hours after injection of kaolin and carrageenan, all animals displayed reduced PWL responses and spontaneous pain-related behaviors. In the group infused with gabapentin spinally, the PWL significantly decreased to about 81% of baseline measurements (paired t-test, p<0.01). By 1.5 hours after spinal gabapentin infusion, the PWL measurements returned back to the baseline, and the toes became almost flat.

TABLE 2

Non-arthritic Vs. Arthritic Animals

|  | PWL (sec.) | PWL (% of baseline) | Behavior Score | Circumference (cm) | Circumference (% of baseline) |
|---|---|---|---|---|---|
| Baseline | 11.47 ± 0.56 | 100 | 0 | 5.18 ± 0.04 | 100 |
| Arthritis (4 h) | 8.66 ± 0.56* | 76.42 ± 3.10* | 1.25 ± 0.13* | 5.92 + 0.09* | 114.38 ± 1.86* |

*p < 0.01.

TABLE 4

Effects of Gabapentin Administered After Inflammation

| Groups | PWL or Circumference (% of control) | PWL (after 4 h arthritis) | PWL (after 5.5 h arthritis) | Behavior Score (after 5.5 h arthritis) | Circumference (after 5.5 h arthritis) |
|---|---|---|---|---|---|
| Gabapentin (spinal cord) (n = 6) | 100 | 80.71 ± 3.23* | 100.85 ± 10.63 | 0.50 ± 0.20 | 122.22 ± 2.32* |
| Gabapentin (subcutaneous) (n = 6) | 100 | 85.05 ± 3.68* | 81.89 ± 4.43* | 1.17 ± 0.29* | 120.66 ± 3.59* |
| aCSF (spinal cord) (n = 6) | 100 | 78.37 ± 5.37* | 78.57 ± 4.38* | 1.17 ± 0.28* | 113.89 ± 3.49* |

*$p < 0.01$.

In the group which was infused with gabapentin subcutaneously, the PWL to noxious radiant heat significantly decreased by 15% from baseline measurements 4 hours after joint injection, and after 1.5 hours drug infusion, the PWL continued to decrease to 82% of the baseline value, similar to aCSF control arthritic rats. Both the pain-related behavior score and the circumference of the inflamed joint increased significantly after 4 hours arthritis and 1.5 hours drug infusion (5.5 h post) for all groups.

The foregoing study establishes that GABA analogs such as gabapentin are effective in both preventing and reversing the affects of kaolin/carrageenan knee joint inflammation on secondary heat hyperalgesia and spontaneous pain-related behaviors. In both treatment groups, the significant finding was the ability of gabapentin to retain (or return) the PWL latency scores to baseline. Its effectiveness in reducing the hyperalgesia and pain-related behavior after the arthritis is fully developed in this model indicates that gabapentin and similar GABA analogs will have clinically useful effects in clinical inflammatory conditions.

What is claimed is:

1. A method for preventing and treating inflammatory diseases comprising administering to a subject in need of treatment an anti-inflammatory amount of a compound of Formulas IIIA, IIIB, or IIIC

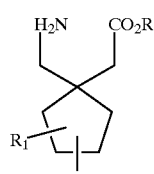

IIIA

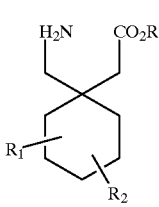

IIIB

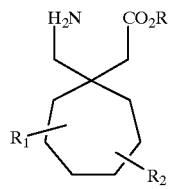

IIIC and pharmaceutically acceptable salts thereof, wherein:
   R is hydrogen or lower alkyl;
   $R_1$ is independently selected from methyl and ethyl; and
   $R_2$ is independently selected from hydrogen, methyl, and ethyl.

2. A method according to claim 1 employing a compound of Formula I

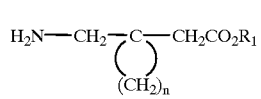

I wherein $R_1$ is hydrogen or lower alkyl and n is an integer of from 4 to 6, and the pharmaceutically acceptable salts thereof.

3. The method according to claim 2 employing gabapentin.

4. The method according to claim 1 employing (1-aminomethyl-3-methylcyclohexyl) acetic acid.

5. The method according to claim 1 employing (1-aminomethyl-3-methylcyclopentyl) acetic acid.

6. The method according to claim 1 employing (1-aminomethyl-3,4-dimethylcyclopentyl) acetic acid.

7. A method according to claim 1 employing a compound of Formula II

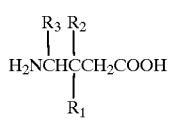

II wherein $R_1$ is a straight or branched alkyl of from 1 to 6 carbon atoms, phenyl, or cycloalkyl of from 3 to 6 carbon atoms;
   $R_2$ is hydrogen or methyl; and
   $R_3$ is hydrogen, methyl, or carboxyl, and the pharmaceutically acceptable salts thereof.

8. The method according to claim 7 employing pregabalin.

9. The method according to claim 7 employing R-(3)-(aminomethyl)-5-methyl-hexanoic acid.

10. The method according to claim 7 employing 3-(1-aminoethyl)-5-methyl-hexanoic acid.

* * * * *

UNITED STATES PATENT AND TRADEMARK OFFICE
CERTIFICATE OF CORRECTION

PATENT NO. : 6,329,429 B1
DATED : December 11, 2001
INVENTOR(S) : Schrier et al.

It is certified that error appears in the above-identified patent and that said Letters Patent is hereby corrected as shown below:

Column 12,
Line 35, cancel beginning with "2. A method according to Claim 1 employing a compound" to and including "salts thereof."
Line 45, and insert instead the following claim:

2. A method for preventing and treating inflammatory diseases comprising administering to a subject in need of treatment an anti-inflammatory amount of a compound of Formula I

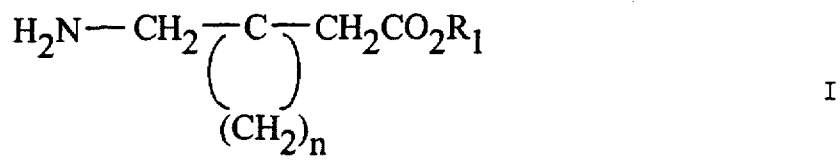

I wherein $R_1$ is hydrogen or lower alkyl and n is an integer of from 4 to 6, and the pharmaceutically acceptable salts thereof.
Line 53, cancel beginning with "7. A method according to claim 1 employing a compound" to and including "tically acceptable salts thereof."
Line 67, and insert instead the following claim:

7. A method for preventing and treating inflammatory diseases comprising administering to a subject in need of treatment an anti-inflammatory amount of a compound of Formula II

II

UNITED STATES PATENT AND TRADEMARK OFFICE
CERTIFICATE OF CORRECTION

PATENT NO. : 6,329,429 B1
DATED : December 11, 2001
INVENTOR(S) : Schrier et al.

It is certified that error appears in the above-identified patent and that said Letters Patent is hereby corrected as shown below:

wherein $R_1$ is a straight or branched alkyl of from 1 to 6 carbon atoms, phenyl, or cycloalkyl of from 3 to 6 carbon atoms;
$R_2$ is hydrogen or methyl; and
$R_3$ is hydrogen, methyl, or carboxyl, and the pharmaceutically acceptable salts thereof.

Signed and Sealed this

Twenty-third Day of April, 2002

*Attest:*

*Attesting Officer*

JAMES E. ROGAN
*Director of the United States Patent and Trademark Office*